United States Patent
Schiferli

(10) Patent No.: US 9,038,481 B2
(45) Date of Patent: May 26, 2015

(54) APPARATUS CONFIGURED TO DETECT A PHYSICAL QUANTITY OF A FLOWING FLUID, AND A RESPECTIVE METHOD

(75) Inventor: Wouter Schiferli, The Hague (NL)

(73) Assignee: Nederlandse Organisatie voor toegepast-natuurwetenschappelijk onderzoek TNO, Delft (NL)

(*) Notice: Subject to any disclaimer, the term of this patent is extended or adjusted under 35 U.S.C. 154(b) by 375 days.

(21) Appl. No.: 13/500,933

(22) PCT Filed: Oct. 8, 2010

(86) PCT No.: PCT/NL2010/050662
§ 371 (c)(1),
(2), (4) Date: Jun. 19, 2012

(87) PCT Pub. No.: WO2011/043667
PCT Pub. Date: Apr. 14, 2011

(65) Prior Publication Data
US 2012/0266689 A1    Oct. 25, 2012

(30) Foreign Application Priority Data
Oct. 8, 2009  (EP) .................... 09172580

(51) Int. Cl.
*G01F 1/32* (2006.01)
*G01N 9/00* (2006.01)

(52) U.S. Cl.
CPC ............ *G01F 1/3227* (2013.01); *G01F 1/3245* (2013.01); *G01N 9/002* (2013.01)

(58) Field of Classification Search
CPC ... G01F 1/3227; G01F 1/3245; G01F 15/002; G01N 9/002
USPC .......................................... 73/861.18, 861.24
See application file for complete search history.

(56) References Cited

U.S. PATENT DOCUMENTS

| 4,281,553 | A |   | 8/1981  | Datta-Barua |          |
|-----------|---|---|---------|-------------|----------|
| 5,152,181 | A | * | 10/1992 | Lew ......... | 73/861.24 |
| 7,152,460 | B2| * | 12/2006 | Gysling et al. ... | 73/861.18 |

(Continued)

FOREIGN PATENT DOCUMENTS

| DE | 4316067        |    | 11/1994  |            |
|----|----------------|----|----------|------------|
| DE | 102005050400   |    | 4/2007   |            |
| EP | 1936332        |    | 6/2008   |            |
| JP | 58219417 A     | *  | 12/1983  | G01F 1/32  |
| WO | 02/077613      |    | 10/2002  |            |
| WO | WO 2008078996 A1 | * | 7/2008 |            |
| WO | WO 2008078996 A9 | * | 8/2008 |            |

OTHER PUBLICATIONS

English Machine Translation of DE 102005050400 to Kahlert et al. Apr. 26, 2007.*

(Continued)

*Primary Examiner* — Lisa Caputo
*Assistant Examiner* — Philip Cotey
(74) *Attorney, Agent, or Firm* — Banner & Witcoff, Ltd.

(57) ABSTRACT

Apparatus configured detect a physical quantity, for example a density, of a flowing fluid, the apparatus including:
  a sensor body (2) configured to extend into the flowing fluid, the sensor body comprising a fiber Bragg grating (FBG) of a fiber Bragg grating sensor (3, 7, FBG), for generating a detector signal relating to vibration of at least part (2B) of the sensor body (2); and
  a processing unit, configured to process the detector signal, and to determine the physical quantity based on detected vibration at a mechanical eigenfrequency of the flexible part (2B) of the sensor body (2).

29 Claims, 6 Drawing Sheets

(56) References Cited

U.S. PATENT DOCUMENTS 8,234,931 B2 * 8/2012 Cheng et al. ............... 73/861.24
2004/0173731 A1 * 9/2004 Beger et al. .................. 250/226

OTHER PUBLICATIONS

Takashima et al. "A water flowmeter using dual fiber Bragg grating sensors and cross-correlation technique" Sensors and Actuators vol. 116, No. 1, Oct. 4, 2004, ISSN: 0924-4247.*

International Search Report, PCT/NL2010/050662, Mail date: Dec. 8, 2010.
Ping Lu et al: "Fiber Bragg grating sensor for simultaneous measurement of flow rate and direction", Measurement Science and Technology, IOP, Bristol, GB, vol. 19, No. 12, Dec. 1, 2008, p. 125302, XP020144308, ISSN: 0957-0233.
Zhang H et al: "A study of mass flow rate measurement based on the vortex shedding principle", Flow Measurement and Instrumentation, Butterworth-Heinemann, Oxford, GB, vol. 17, No. 1, Mar. 1, 2006, pp. 29-38, XP024960981, ISSN: 0955-5986 [retrieved on Mar. 1, 2006].

* cited by examiner

APPARATUS CONFIGURED TO DETECT A PHYSICAL QUANTITY OF A FLOWING FLUID, AND A RESPECTIVE METHOD

CROSS-REFERENCE TO RELATED APPLICATIONS

This application is a U.S. National Stage application under 35 U.S.C. §371 of International Application PCT/NL2010/050662 (published as WO 2011/043667 A1), filed Oct. 8, 2010, which claims priority to Application EP 09172580.4, filed Oct. 8, 2009. Benefit of the filing date of each of these prior applications is hereby claimed. Each of these prior applications is hereby incorporated by reference in its entirety.

The present invention relates to an apparatus configured to detect a physical quantity, for example a density, of a fluid, for example a gas, a liquid, or a liquid/gas mixture.

BACKGROUND ART

International Patent Application No. PCT/NL2007/050665 discloses an innovative assembly comprising a fluid channel and a flowmeter, and a method to measure a fluid flow rate. The known flowmeter comprises a vortex shedder extending in the channel, the vortex shedder being configured to generate Karman vortices in fluid flowing through the channel during operation. The vortex shedder is provided with a fiber Bragg grating (FBG) of a fiber Bragg grating sensor. During operation, a Karman vortex frequency of the vortices generated by the vortex shedder is detectable utilizing a fiber Bragg grating sensor signal relating to the respective fiber Bragg grating of that vortex shedder. In a further advantageous embodiment, the known flowmeter is configured to detect a temperature, particularly using a fiber Bragg grating, as well.

SUMMARY

The present invention provides an apparatus and method wherein one or more fluid related quantities can be detected accurately, using relatively inexpensive, compact and durable means, without the sensor requiring external power (or electrical signal communication means).

To this aim, according to an embodiment of the invention, the apparatus is characterised by including:

a sensor body configured to extend into the flowing fluid (during operation), the sensor body comprising a fiber Bragg grating of a fiber Bragg grating sensor, for generating a detector signal relating to vibration of at least part of the sensor body; and a processing unit, configured to process the detector signal, and to determine the physical quantity based on detected vibration at a mechanical eigenfrequency of the flexible part of the sensor body.

More particularly, the invention can be defined by the features of claim 1.

The present invention is based on the notion that an aforementioned flowmeter can also be used to measure the density of the flowing fluid, or another fluid related quantity, such as its mass or a mass flow rate. Particularly, it has been found that the flowing fluid can induce natural mechanical vibrations of a sensor part, at one or more respective mechanical eigenfrequencies (see FIG. 9 of this patent application). A FBG of the flowmeter provides a low cost, accurate and reliable means to detect such vibrations. Preferably, the sensor body integrally comprises the fiber Bragg grating.

FIG. 9 provides evidence of the simultaneous occurrence of Karman vortex induced vibrations and eigenfrequency vibrations of the sensor body part. It is believed that the mechanical eigenfrequency vibration is simply excited by turbulent fluctuations naturally present in the flow, and not necessarily by vortex shedding.

Generally, during operation, the processing unit will be located separate from the sensor body. One or more optical communication means, for example one or more fibers, can be applied to communicate the (optical) detector signal between the sensor body and the processing unit. Thus, the resulting device is very well adapted for use in down-hole applications, since the sensor part does not require any electric power, nor electric signal communications (for example to an optional data processor located at a distance at a suitable location).

Particularly, the processing unit is configured to detect said mechanical eigenfrequency (using said detector signal). It should be observed that detection of a particular frequency from a sensor signal as such, for example the frequency peak (that is associated with the eigenfrequency) in the spectrum of the signal, is common general knowledge to the skilled person in the field of sensors signal processing.

Detecting said mechanical eigenfrequency can be achieved in various ways. The processing unit can be configured to process the detector signal to obtain a frequency spectrum of the signal. It is commonly known that this can be done by performing spectral analysis on a time signal obtained from the detector. This may include, but is not limited to, Fourier spectral analysis. The resulting spectrum will contain a frequency peak that corresponds to the eigenfrequency. The actual frequency at which this peak occurs is influenced by the density of the surrounding fluid, which shifts this frequency from a base value which would occur in a vacuum (an initial natural eigenfrequency). It is common knowledge that this base frequency can be obtained from experiments or theory. Knowing this base frequency, the density of the surrounding medium can be deduced by measuring the frequency at which the shifted peak occurs.

It follows that in a further embodiment, the following formula is used by the processing unit to determine said physical quantity of the fluid:

$$f = f_0 \cdot (1 + CK \cdot rho)^{-1/2}$$

wherein f is the detected (actual) eigenfrequency (Hz) of the sensor body part in the fluid, $f_0$ is an initial natural eigenfrequency (Hz) of the part in vacuum, rho is the density of the fluid (kg/m$^3$) and CK is a constant (m$^3$/kg) associated with the dimensions and mass of the part.

Most advantageously, the present invention is integrated with a flow rate measurement functionality. It has been found that the same apparatus can be used to simultaneously detect fluid flow rate, particularly by detecting a vortex shedding frequency, and fluid density (or mass) by detecting one or more mechanical eigenfrequencies (wherein the eigenfrequency or eigenfrequencies is/are separate from the vortex shedding frequency during operation).

Particularly, as follows from FIG. 9 (see below), the vibrations that are associated with said eigenfrequency occur at a higher frequency value than the value of a vortex shedding frequency, and can therefore detected in a straightforward manner by the processing unit.

In an advantageous embodiment, the sensor body is a vortex shedder that is configured to generate Karman vortices in the fluid during operation. In that case, a very compact configuration can be achieved when a Karman vortex frequency of vortices generated by the vortex shedder is detectable utilizing a fiber Bragg grating sensor signal relating to a respective integral fiber Bragg grating of the vortex shedder. Also, preferably, the sensor body may have a flexible part that integrally comprises an at least partly curved fiber part, extending at least partly along a curved path and containing the fiber Bragg grating. In that case, preferably, a first section of the fiber part may be spaced-apart from a rigid sensor body part (holding the flexible part), for example in a substantially orthogonal direction with respect to a fluid flow path. A second section of the fiber part may be located near the rigid part, for example extending substantially parallel with respect to a fluid flow path. The second section of the fiber part can contain the fiber Bragg grating, to detect the eigenfrequency vibrations.

Also, there is provided a method of detecting a physical quantity, for example a fluid density, of a flowing fluid, for example using the apparatus according to the invention, wherein the fluid induces vibration of a flexible part of a sensor body at an eigenfrequency, detecting the eigenfrequency, and processing the detected eigenfrequency to measure the physical quantity. For example, but not necessarily, the fluid flow induced eigenfrequency vibration can be a mechanical first mode eigenfrequency vibration.

For example, in a method according to the invention, the fluid induces vibration of the flexible part of the sensor body at a (relatively low) first frequency, wherein an eigenfrequency of that (vibrating) part is being detected, the eigenfrequency being separate from the first frequency, wherein the detected eigenfrequency is processed to determine the physical quantity.

For example, it has been found that application of a relatively thin (plate-like) resilient sensor part can provide low frequency eigenmode vibrations of that part, simultaneously with but separate from a first (Karman vortex) frequency of that part.

Further advantageous embodiments of the invention are described in the dependent claims. These and other aspects of the invention will be apparent from and elucidated with reference to non-limiting embodiments described hereafter, shown in the drawings.

Similar or corresponding features are denoted by similar or corresponding reference signs in the present application.

FIGS. 1-7 depict a non-limiting embodiment of an assembly comprising a fluid channel C and a flowmeter 1.

The fluid channel C (for example a fluid line, pipe, conduit) can be configured to conduct a fluid, for example a gas, gas mixture, liquid, liquid mixture, water, steam. In a particular embodiment, the channel C can be arranged to inject fluid into a oil or gas field, however, to skilled person will appreciate the channel C can be used in many other applications. In the present embodiment, the channel C has a substantially circular cross-section having a diameter (width) W. The channel can also have different configurations, for example having a rectangular or square cross-section, or a different cross-section, as will be appreciated by the skilled person.

The flowmeter 1 is configured to measure fluid flow rate of fluid flowing through the channel C during operation. To this aim, the flowmeter 1 comprises at least one vortex shedder 2 (only one being shown in the present drawings) extending in the channel C. In a further embodiment the assembly has a plurality of spaced-apart vortex shedders 2, to detect flow rates at different locations in the channel C. In that case, flow rate profiles can be detected with the flowmeter 1, for example to determine or estimate amounts of fluid that are being injected in certain parts (layers) of an oil or gas field.

Advantageously, as will be described below, it has been found that the flowmeter 1 can also be used to detect a physical quantity, for example a density, of a flowing fluid, flowing through the channel C. To that aim, natural mechanical frequencies ($f_n$) of a shedder part are being detected.

Figure 3:
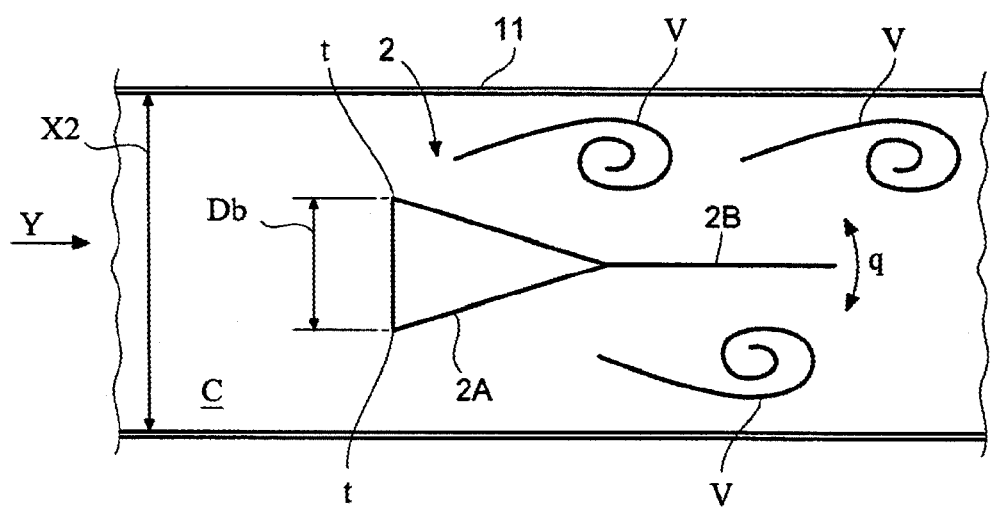
FIG. 3 shows a longitudinal, schematic, cross-section over line III-III of FIG. 1.

Each vortex shedder 2 is configured to generate Karman vortices V in fluid flowing through the channel C during operation (see FIG. 3). A fluid flow direction is indicated in FIG. 3 by arrow Y. Particularly, each vortex shedder 2 comprises a bluff body 2, having two vortex separation edges t, preferably substantially parallel, sharp lateral edges. The bluff body 2 can be arranged to have these edges t located at upstream positions with respect to a remaining bluff body part (as in FIG. 3), or alternatively at downstream positions (for example, in case the flow direction in FIG. 3 has been reversed). In the present embodiment, the bluff body 2 is rigidly attached to a channel wall 11.

Particularly, the flow meter 1 is based on the principle of vortex shedding on an obstacle (bluff body 2) placed in the flowing fluid (see FIG. 3). A boundary layer can grow on both sides of the bluff body 2 because of viscosity and can separates at separation points, provided by the edges t. During operation, the vortices V can separate alternately on both sides of the body 2, with a vortex shedding frequency $f_K$. As is known from the prior art, the vortex shedding frequency $f_K$ is proportional to the flow velocity U, according to the following equation 1:

$$f_K = St(U/D_b) \quad (1)$$

wherein St is the dimensionless Strouhal number, U is the flow velocity (m/s) and $D_b$ is the diameter/width of the bluff body (m). As is commonly known, the Strouhal number St is characteristic for a certain bluff body shape and is constant in a relatively large range of the Reynolds number, so that the relation between flow rate (m/s) and shedding frequency is linear over a wide flow rate range. For example, the present embodiment can be used in the case of flow velocities are in the range of 0.5 to 5 m/s (turndown 1:10), and for example can have operation temperatures ranging from 20 to 350 degrees Celsius, at various operating pressures. Also, the meter 1 can be configured to be used outside these velocity and temperature ranges, as will be appreciated by the skilled person. The boundary layer can be controlled by choosing the shedder body 2 on which the separation points are defined exactly, by introducing sharp edges t on the body 2.

The bluff body 2 can be made of various materials. For example, the bluff body 2 can be made of rigid, corrosive resistant material, particularly a suitable metal, alloy, steel or rigid plastic, reinforced plastic, for example stainless steel, or aluminium (stainless steel is preferred for downhole applications for durability reasons), and/or other suitable materials.

FIGS. 4-7 show an advantageous embodiment of a bluff body/shedder configuration in more detail. To have a linear relation between the flow velocity and the vortex shedding, the present vortex shedding body 2 provides well-defined separation lines (edges) t, and has a substantially T-shaped cross-section. To this aim, particularly, the shedder 2 has been provided with a first part 2A (i.e. the top of the T of the T-shape) and a second part 2B (i.e. the centre line of the T of the T-shape), the first part having the two separation edges t and the second part being a fluid dividing element 2B.

Both the first and second shedder body parts 2A, 2B can have various configurations. The first and second shedder part 2A, 2B are preferably made of the same material, however, this is not necessary.

Advantageously, the first shedder body part 2A is a rigid, preferably substantially solid part 2A that is rigidly fixed (i.e. substantially unmovably during operation) to the wall 11 of the channel C. The first shedder body part 2A comprises a front surface, extending substantially transversally with respect to a longitudinal channel direction (i.e. flow direction Y of fluid flowing through the channel C during use), wherein the lateral sides of the front surface are the vortex separation lines t of the shedder 2.

In the present embodiment, the length L1 of the first shedder body part 2A is substantially or nearly equal to the flow channel diameter/width X1 (see FIG. 1), so that the walls of the channel C act as end plates for the flow separation edges t (i.e., opposite ends of each flow separation edge t are located at or close to respective channel wall parts of channel wall 11). Thus, the first part 2A of the bluff body 2 extends from a first inner wall part 11a of the channel C to an opposite second inner wall part 11b of the channel C, as in FIG. 1-2, and preferably centrally through the channel C. Herein, for example, a narrow slit can still extend between an end of the bluff body 2 and the channel wall, for example a slit H having a width of about 1 mm or smaller as has been indicated in FIG. 3.

In another embodiment, the width of each slit H can be larger than 1 mm, for example larger than 1 cm.

For example, in a durable configuration, the first shedder body part 2A can be firmly fixed at one end (or alternatively at both ends) to a channel wall part (or wall parts), for example by clamping, adhesive, welding, suitable couplings, bolting, detachably, a combination thereof, and/or in a different manner. In the present embodiment, one end of the first shedder body part 2A is attached to a mounting structure 9 that has been firmly joined to the first channel wall part. For example, the mounting structure can include a first mounting part 9a to hold the bluff body 2, a second mounting part 9b that is attached to the first part 9a via three first bolts 13a, being spaced-apart from each other in a triangle configuration, and a third mounting part 9c that interconnects the mounting second part 9b to the channel wall 11. Besides, the channel wall 11 can comprise an opening 12 for introducing the bluff body 2, being held by the first mounting part 9a, into the channel C. The mounting structure 9 can be configured to provide a fluid tight sealing of the opening 12 after mounting.

In another embodiment, the length L1 of the respective bluff body part 2A, can be significantly smaller than the flow channel diameter/width X1. Optionally, the bluff body 2 can comprise one or more end plates, extending laterally with respect to the vortex separation edges t, for controlling the boundary layer on the bluff body 2.

Figure 1:
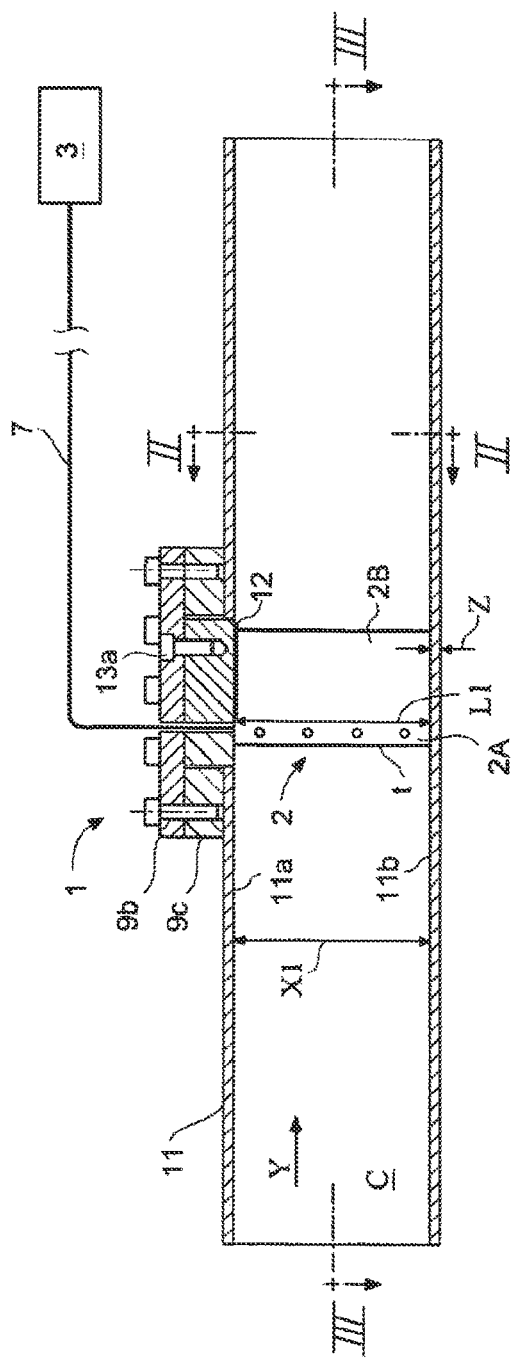
FIG. 1 depicts a longitudinal cross-section of an embodiment of the invention.
Figure 2:
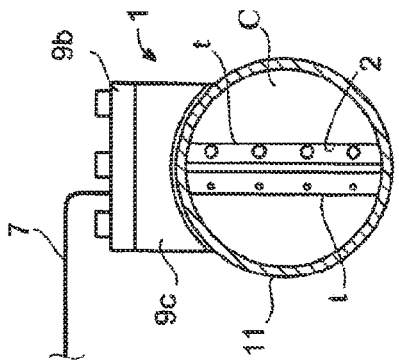
FIG. 2 depicts a cross-section over line II-II of FIG. 1.

In a further embodiment (see FIG. 3), the distance $D_b$ between the two vortex separation edges (lines) t, measured transversally with respect to a longitudinal channel direction, is larger than a tenth of a width X2 of the fluid channel C, measured in the same direction, for example about a fourth of the width of the fluid channel C, wherein the mentioned distance $D_b$ between the two vortex separation edges is preferably smaller than half the width X2 of the channel C. Since in the present embodiment, the channel C has a circular cross-section, the last-mentioned channel width X2 is equal to the above-mentioned channel width that is indicated in FIG. 1 with arrow X1.

A longitudinal cross-section of the first shedder body part 2A is preferably substantially triangular (as in FIG. 3, 7) or truncated triangular, or can have another shape.

Preferably, the second shedder part 2B has a panel-like, strip-like or sheet-like configuration, having a substantially rectangular shape (such as in the present embodiment). For example the second shedder part 2B can be dimensioned such in three orthogonal directions, that one orthogonal direction (the thickness k) is significantly smaller (for example by a factor of at least 50) than each of the second and third orthogonal directions (length L2 and width G).

Also, preferably, the second shedder part 2B extends substantially in longitudinal channel direction and has two fluid pressure receiving surfaces, being faced away from each other, that are configured to alternatively receive vortex induced pressure variations during operation (see FIG. 3), and to be strained by those pressure variations. In the present embodiment, particularly, the pressure variations cause a vibration and/or deformation the second shedder part 2B that is perpendicular to the flow direction Y (in other words: vortex induced deformation and/or vibration of the shedder part 2B will mainly be in lateral directions of that part 2B, and is indicated by double arrow q in FIG. 3, i.e. vibration and/or deformation that is substantially perpendicular to the pressure receiving surfaces of that shedder part 2B), the deformation and/or vibration leading to surface strain in the second shedder part 2B.

In the present embodiment, the second shedder part 2B extends centrally with respect to the first shedder part 2A, perpendicularly with respect to the bluff body surface containing the two separation edges t, and preferably centrally through the channel C after mounting. For example, the external contours of the bluff body, including the first and second part 2A, 2B) can be substantially mirror-symmetric with respect to a longitudinal central mirror plan, as in the present embodiment.

Figure 5:
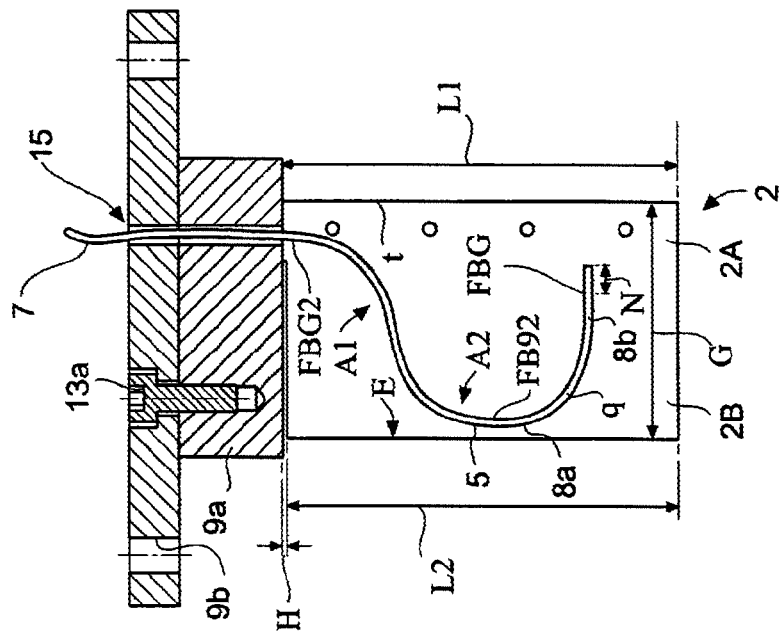
FIG. 5 is a longitudinal cross-section of the shedder shown in FIG. 4.

In the present embodiment, one transversal side (a lower side of that part in FIG. 5A) of the second shedder part 2B extends flush with the respective side of the first shedder part 2A (see FIG. 5). The other transversal side of the first shedder part 2B, however, is spaced-apart from the mounting structure 9 (see FIG. 5), the distance there-between being indicated by an arrow H in FIG. 5.

The second shedder part 2B is a pressure variation receiving part 2B, or straining part, that is configured to receive vortex induced pressure variations during operation. Particularly, the Karman vortices can induce strain variations in the second shedder part 2B (indicated by the arrow q in FIG. 3), and more particularly in surface parts thereof (i.e. vortex induced pressure variations during operation lead to surface strain in/of the second shedder part 2B). For example, the second shedder part 2B can be slightly elastically deformable during operation, such that this shedder part 2B performs small oscillations q during operation due to receiving vortex related pressure variations, the small oscillations q leading to a varying straining of the two lateral (pressure receiving) surfaces of the second shedder part 2B. It has been found that these strain variations are particularly relatively high at a region that abuts the first shedder part 2A (i.e. a junction with the first shedder part 2A).

In a further embodiment, the second part 2B of the shedder 2 comprises two transversal sides that are spaced-apart from opposite longitudinal flow restriction parts (that include a channel wall part for one transversal shedder side, and a mounting structure part for the other transversal shedder side, in the present embodiment). For example, in FIG. 1, a distance Z between the (in the drawing) lower transversal side of the rectangular vortex shedder part 2B and the channel wall 11 is preferably in the range of about 0.1-10 mm, particularly about 1-2 mm, and the width H of the slit between the (in FIG. 1) upper transversal side of the rectangular vortex shedder part 2B and a surface of the first mounting part 9a is also preferably in the range of about 0.1-10 mm, particularly about 1-2 mm.

In another embodiment, the width of the slit H between the upper transversal side of the rectangular vortex shedder part 2B and a surface of the first mounting part 9a can be larger than 10 mm.

Therefore, the transversal sides of the second shedder part 2B are free from opposite flow restricting surfaces, such that vortex induces pressure variations can lead to surface strain variations in and/or oscillations of the second shedder part 2B. Particularly, the vortex induced pressure variations can induce vibration and/or deformation of the vortex shedder, which vibration and/or deformation can cause the surface strain.

According to an embodiment, the length L2 of the second shedder part 2B (measured in parallel direction with respect to the separation lines t) can be slightly smaller than the length L1 of the first shedder part 2A, the difference in length being for example in the range of about 0.1-20 mm, particularly in the range of about 1-2 mm (see FIG. 5).

The length L2 of the second shedder part 2B can be larger than a width G of an external section (tail section) of that part 2B, the width G being measured in longitudinal channel direction (see FIG. 5; herein, the width G of the second shedder part 2B is the width of the section of that part that extends externally from the first shedder part, and serves as a fluid pressure variation receiving section of the shedder). For example, the length L2 of the second part 2B can be in the range of about 1.5-2 times the mentioned width G of that part 2B. Good results have been found in the case that L2 is in the range of 1.7-1.9 times G, particularly length L2 equals the width G multiplied by 1.8.

In another embodiment, the length L2 of the second shedder part 2B can be the same as or smaller than the width G of the external section (tail section) of that part 2B, the width G being measured in longitudinal channel direction In that case, for example, the length L2 of the second shedder part 2B can be in the range of about 0.5-1 times the mentioned width G of that part 2B.

Figure 7:
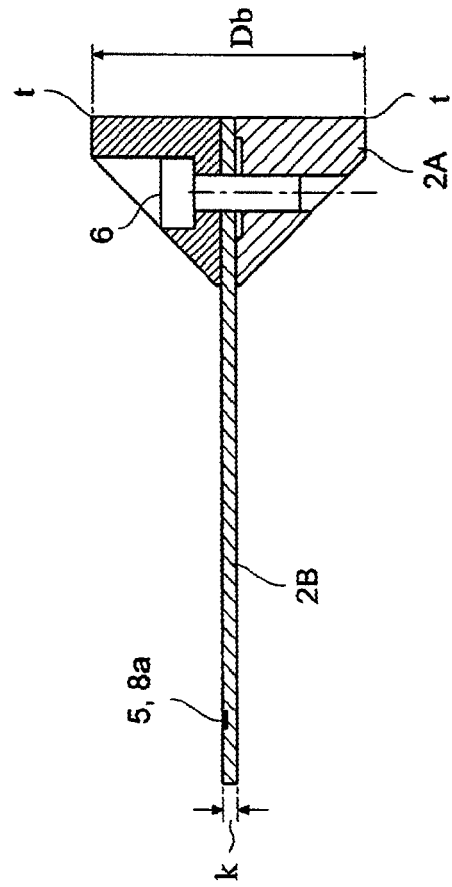
FIG. 7 is a cross-section over line VII-VII of FIG. 6.
Figure 6:
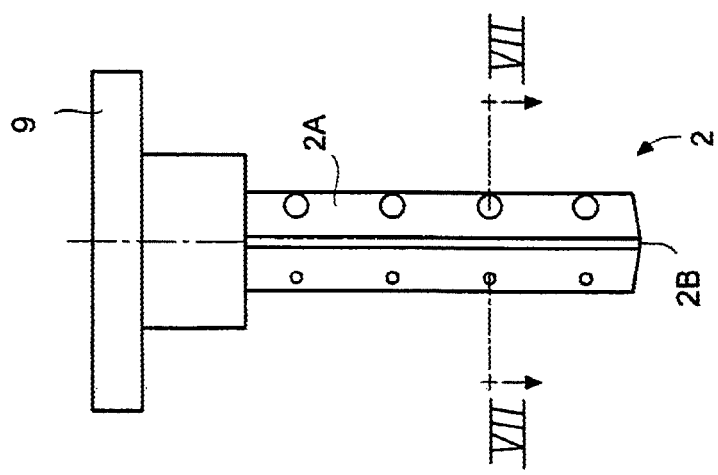
FIG. 6 is a front view of the shedder of FIG. 4.

Also, it has been found that good results can be obtained in the case that a thickness k of the second shedder body part 2B (measured in its transversal direction) is smaller than about 10 mm, preferably smaller than about 5 mm (see FIG. 7).

The first and second shedder parts 2A, 2B can be joined to each other in various ways. For example, the first and second shedder parts can be made in one piece. Also, first and second shedder parts 2A, 2B can be interconnected with adhesive, welding, bolting (as in the FIG. 1-7 embodiment, with bolts 6), clamping, force closure fixation, form closure fixation, a combination thereof and/or in a different manner. In the present embodiment, the second shedder part 2B comprises an internal section that extends in the first shedder part 2A to be held thereby, and the above-described external section (having the mentioned width G) that extends outside the first shedder part 2A to perceive vortex induced pressure variations. Preferably, as follows from the drawing, the mentioned external (tail) section of the second shedder part 2B is substantially uninterrupted, providing substantially uninterrupted (continuous) pressure receiving surfaces.

Preferably, the first and second shedder parts 2A, 2B are configured such that relatively vortex pressure variations can induce relatively large strain variations into a certain area of the shedder (for example the external section of the second shedder part 2B that abuts the first shedder part 2A).

Also, each vortex shedder 2 is provided with a first fiber Bragg grating FBG of a fiber Bragg grating sensor 3, 7, FBG. During operation a Karman vortex frequency $f_K$ of the vortices V generated by the vortex shedder 2 is detectable utilizing a fiber Bragg grating sensor signal relating to the respective first fiber Bragg grating FBG of that vortex shedder 2. Preferably, the first fiber Bragg rating FBG is attached to the section of shedder 2 that experiences relatively large surface strain variations due to vortex pressure variations induced vibration/deformation during operation, and is configured to detect those strain variations.

Also, in a further embodiment the fiber Bragg grating FBG of the respective vortex shedder 2 is arranged to perceive the mentioned pressure variations, particularly via pressure variation induced strain variations of the pressure variation receiving part 2B of the shedder 2, and to vary the respective fiber Bragg grating sensor signal as a result of perceiving the pressure variations. Preferably, the fiber Bragg grating FBG is mounted close to, or extends in, abuts, or is embedded in, a pressure receiving surface of the second shedder part 2B, to be sensitive to the mentioned surface strain that is caused by the deformation/vibration of that shedder part 2B during operation.

Advantageously, the first fiber Bragg grating FBG is spaced-apart from a vortex separation surface (which surface contains the two vortex separation lines t) of the respective vortex shedder 2. Also, preferably, the location of the first fiber Bragg grating FBG is spaced-apart from the two transversal sides of the second shedder part 2B.

Besides (a follows from FIG. 5), a longitudinal direction of the first fiber Bragg grating FBG preferably encloses an angle smaller than 90° with a fluid flow direction during operation, for example an angle smaller than 30° and preferably an angle smaller than 5°. In the present embodiment, the angle between the longitudinal direction of the first fiber Bragg grating FBG and the fluid flow direction Y is about 0°.

Figure 4:
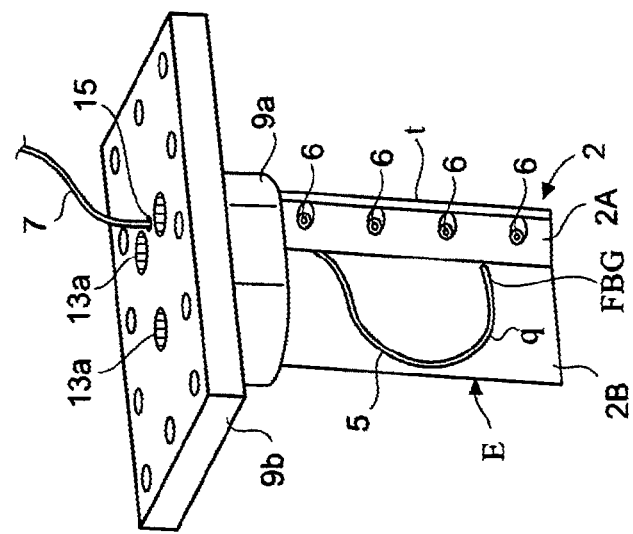
FIG. 4 is a perspective view of a vortex shedder of the embodiment of FIG. 1.

Particularly, the pressure variation receiving part/second shedder part 2B integrally comprises a curved fiber part 8, extending at least partly along a curved path and containing the first fiber Bragg grating FBG (see FIG. 4-5). A first section 8a of the curved fiber part 8 preferably extends a short distance from a free shedder edge E that is faced away from a vortex shedding surface of the vortex shedder 2, in a substantially orthogonal direction with respect to a longitudinal channel direction (see FIG. 5). A second section 8b of the fiber part 8 is preferably located near a vortex shedding surface of the vortex shedder 2 and extends substantially parallel to the longitudinal channel direction. In the present embodiment, this second fiber section 8b comprises the first fiber Bragg grating FBG. Particularly, the curved path of the fiber part, being provided on/in the shedder 2, comprises a first bend A1 to lead the fiber from an entry location at the first shedder part 2A towards the free shedder edge E, and a subsequent second bend A2 (having a bend direction that is opposite to the bend direction of the first bend) to lead the fiber from the free shedder edge E back to the first shedder part 2A to a Bragg grating location that is spaced-apart from the entry location.

In a further embodiment (not shown) the fiber can be bended further (for example to make a substantially full loop along and/or through the vortex shedder 2), and can be guided back towards the channel wall 11 and through the holding structure 9, for example to be led to another vortex shedder 2 to provide another first Bragg grating in/at that other shedder 2. In that case, fiber the entry location (point) can also provide a fiber exit location.

Particularly, in the present embodiment, the mounting structure 9 comprises a through-hole 15 (see FIG. 5) to pass the fiber 7 from an area outside the channel C to the vortex shedder 2. The first shedder part 2A can comprise a similar aperture to receive part of the fiber 7. The second shedder part 2B can comprise a curved groove 5 or aperture to hold the curve fiber part 8 containing the first fiber Bragg grating FBG. I a further embodiment, the through-hole 15 can also be used to guide the fiber 7 from the vortex shedder 2 again out of the channel, through the channel wall 11, to another location, for example to another vortex shedder (not shown).

For example, the fiber receiving groove 5 of the shedder 2 can have a depth smaller than the thickness k of the second shedder part 2B, for example a depth smaller than 1 mm, for example about 0.4 mm. For example, depth of the fiber receiving groove 5 can be smaller than half the thickness k of the second shedder part 2B to locate the grating FBG close to and/or in a lateral surface of that part 2B. Preferably, the curved fiber part 8 is substantially embedded in the respective shedder part 2B. The optical fiber part 8 having the Bragg grating FBG can be attached to the respective groove 5, using a suitable adhesive, for example a thermally curable resin, epoxy, or other type of adhesive. Preferably, the fiber receiving groove 5 is configured to hold the respective fiber part substantially snuggly. In a non-limiting embodiment, a width of the groove 5 can be about 1 mm.

Similarly, the assembly can be of a modular configuration, wherein the assembly can include a plurality of vortex shedders 2, each shedder 2 preferably being provided with a mentioned first fiber Bragg grating FBG of the fiber Bragg grating sensor. In that case, a single fiber 7 can simply be provided with all of the first fiber Bragg gratings FBG of the various shedders 2, wherein the fiber 7 can extend from one shedder to the other to transmit the sensors signals.

The operation of a fiber Bragg grating sensor as such is known to the skilled person. In an embodiment, each fiber Bragg grating FBG is configured to substantially reflect one specific wavelength of an optical signal, being transmitted towards the grating FGB through the fiber 7, and to substantially transmit all other wavelengths. Herein, the wavelength of the reflected light depends on the variation of the refractive index in the grating FBG. The reflected wavelength is called the Bragg wavelength $\lambda_b$ and given by:

$$\lambda_b = 2n_{eff} \cdot \Lambda \quad (2)$$

wherein $n_{eff}$ is the effective refractive index of the optical mode propagating in the fiber 7, and is the period $\Lambda$ of the grating. Strain, temperature and pressure can change the properties of the fiber, and thus the reflected wavelength $\lambda_b$. For example, the amplitude of the sensor signal is a measure of the amount of strain experienced by the grating FBG during operation. In the present embodiment, particularly, the reflected wavelength is used as a measure of the flow velocity, wherein the changes of that wavelength are being detected (i.e. reflected sensor signal amplitude changes), which can be achieved in a relatively simple manner, to determine the above-mentioned Karman frequency $f_K$.

For example the fiber 7 can be a standard optical fiber with one or more Bragg gratings FBG, having a minimum bending radius of about 2 to 3 cm and a grating length N (see FIG. 5), for each Bragg gratings FBG, of approximately 2 cm. As will be appreciated by the skilled person, the fiber 7 can also have a smaller bending radius and/or a shorter grating. For example, advantageously, the length N of the first fiber Bragg grating can be about 1 cm.

In the present embodiment, the first grating FBG is principally used to detect a varying strain in/of the vortex shedder 2, wherein a resulting change in the respective sensor signal can be processed to determine the flow velocity U of the fluid. A preferred location for the first grating FBG is on the beginning of the tail part 2B of the shedder 2, immediately behind the (truncated triangle) second shedder part 2A (see FIGS. 5, 7) since it has been found that during operation, the Karman vortex induced strain variations will be largest on this section of the tail shedder part 2B.

Preferably, the whole first grating FBG can be substantially homogeneously strained during operation, which is achieved by positioning the grating FBG substantially parallel to the longitudinal channel direction. However, in practice, in the present embodiment, the strain does not have to be wholly constant over the whole fiber to obtain accurate measurement results. This is because frequency (i.e. the variation of the amplitude, and not the amplitude as such) is the measured parameter, so that amplitude variations of a detected reflected signal do not effect the outcome of the flow measurement. This is contrary to the device shown in JP200387451, in which case the sensor amplitude signal, of the reflected signal, can have a relatively large error due to inhomogeneous straining of the grating.

The present assembly can include a suitable sensor system 3 (for example comprising one or more suitable processors and/or analyzers), for example a commercially available system of the company Deminsys Commercial, the sensor system being optically coupled to the optical fiber 7. The sensor system (i.e. "processing unit") 3 can be configured to generate and transmit an optical signal into the fiber 7, the signal having a wavelength (i.e. the above-mentioned Bragg wavelength) to be at least partly reflected by the first fiber Bragg grating FBG in the case that the grating is being subjected to a predetermined amount of strain, for example no strain. In the case that the assembly includes different fiber gratings FBG having different Bragg wavelengths $\lambda_b$, the optical signal can be multiplexed with different signal parts having these different Bragg wavelengths $\lambda_b$, such that the different gratings FBG can be used independently from each other and at the same time, by the sensor system 3.

Also, the sensor system (processing unit) 3 can be configured to detect the optical signal that is reflected by each first fiber Bragg grating FBG of the vortex shedder(s) 2, and to process the detected optical signal(s), for example to determine the fluid flow rate from the variations of the detected signal(s).

Below, a further advantageous application of the sensor system 3 (or "processing unit") will be explained, relating to detection of a physical quantity, for example a density, of the fluid. To this aim, preferably, the sensor system 3 is configured to detect actual natural (mechanical) vibrations of part 2B of the vortex shedder 2, utilizing said optical signal (the processing including: processing the detected optical signal to detect the frequency of variations of the detected signal, the variations being the result of the varying strain that is being experienced by the grating FBG, to determine a value of an instantaneous eigenfrequency vibration of the shedder part 2B).

During operation of the embodiment of FIGS. 1-7, the fluid flow will induce a vortex shedding at the shedder 2, which will cause pressure fluctuations on the tail part 2B of the bluff body 2. Because of the pressure fluctuations, the tail will be induced to oscillate, which will lead to fluctuating surface strain of the tail part 2B and thus strain fluctuations of the integral first fiber Bragg grating FBG (being preferably mounted on or close to the respective surface of the second shedder part 2B, to measure that surface strain). The surface strain as result of these oscillations will be measured. This can be simply achieved by the sensor system 3 transmitting an optical signal having the Bragg wavelength FBG of the first fiber Bragg grating of the vortex shedder 2 into the fiber 7, and detecting the respective optical signal that is reflected by the first fiber Bragg grating FBG. The detected optical signal is then processed to detect the frequency of variations of the detected signal (the variations being the result of the varying strain that is being experienced by the grating FBG), to determine the fluid flow rate from those variations using above equation 1. As will be explained below, in an advantageous embodiment, the detected optical signal is processed by the sensor system 3 to detect a frequency of variations of the detected signal (the variations being the result of the varying strain that is being experienced by the grating FBG), to determine a physical quantity of the fluid.

Thus, a single FBG sensor is applied to detect the flow rate at a certain location in the fluid channel C, wherein—for example—no complex cross-correlation of different grating sensor signals has to be carried out.

Figure 8:
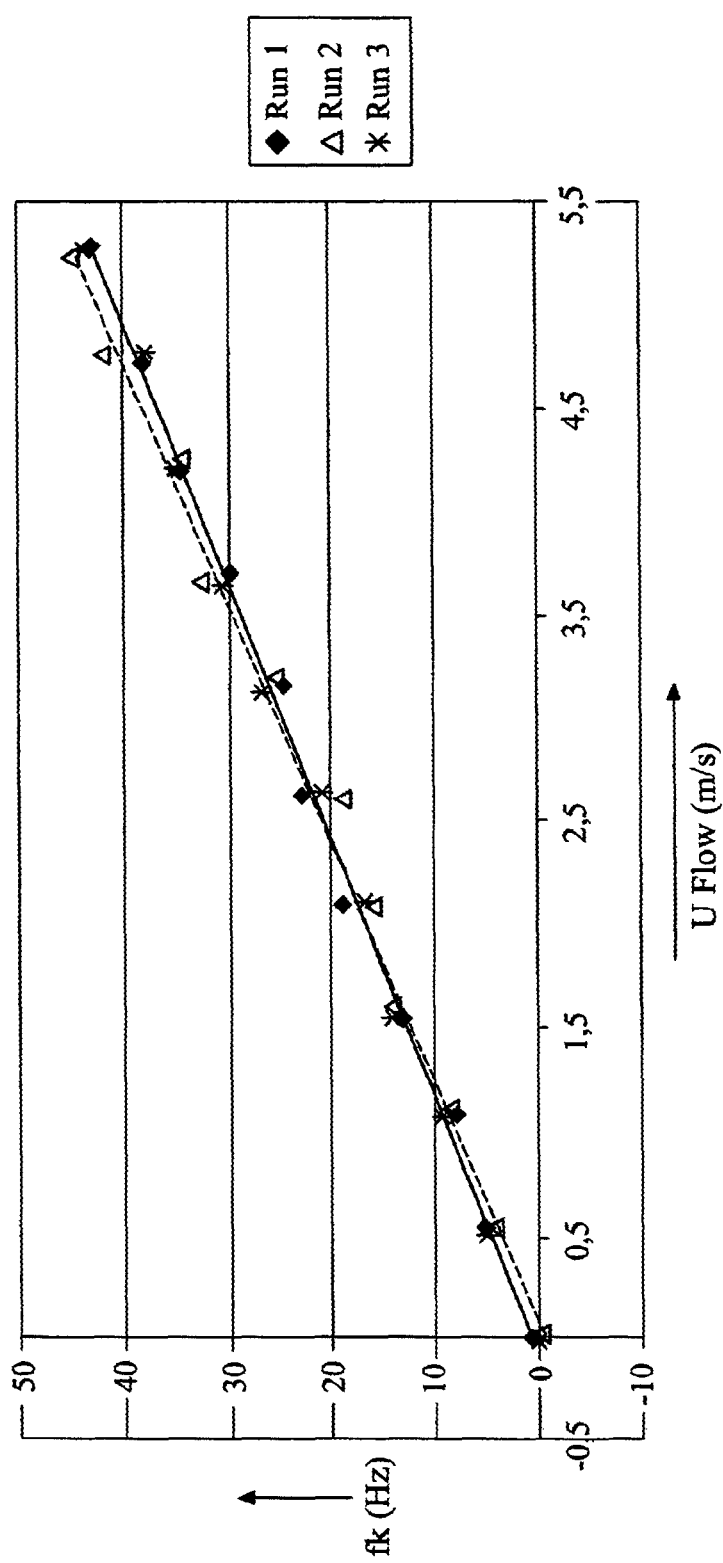
FIG. 8 shows a graph of measured shedding frequency with respect to flow speed, of an example.

FIG. 8 shows a graph of measured shedding frequency $f_K$ with respect to flow speed, of experiments performed with the present embodiment. In this experiment, a flow speed $U_{flow}$ of fluid flowing through the channel C has been set to 11 different predetermined values (from 0 m/s to 5.5 m/s with 0.25 m/s steps) and the resulting FBG sensor signal was being processed to detect the Karman frequency. As follows from FIG. 8, three different test runs all provided the same linear graph of detected frequency $f_K$ versus the flow speed $U_{flow}$. Reliable data can be obtained for low flow rates (0.5 m/s in the present example) as well as high flow rates (5.5. m/s in the present example).

From the above it follows that the present application provides a fiber optic vortex flow meter 1, wherein, in an embodiment, strain resulting from vortex shedding can be measured using a Fiber Bragg Grating (FBG) sensor. This sensor can use a relatively small section of a standard optical fiber 7, so that no downhole electronics are necessary, since the sensor signal can be fed directly to the surface. Flow meter parts that are located in the fluid flow (for example the bluff body 2) particularly do not include any electrically powered components, no electrically operating sensors, and no electric wiring. Preferably, only optical communication means, in this case the (single) optical fiber 7, extends to and through the sensor part(s) located in the fluid. In a further embodiment, the distal section of the sensor part(s) is/are shielded from the interior of the fluid channel C (for example by being embedded in the second shedder part 2B).

The advantages of a fiber optic flow meter are that the meter is intrinsically safe and immune to electromagnetic interference. The bluff body 2 can be substantially T-shaped, comprising a truncated triangle part 2A with a long tail part 2B attached to it. The tail part 2B of this body is preferably made as thin as possible, to increase its deformation and therefore the strain measured with the sensor. The flow meter 1 can detect single phase flows (liquid or gas), for example water, steam, or other fluids.

It has been found that the present embodiment can provide an optimal bluff body design with regard to the linearity of the measurement and to the signal quality, wherein the FBG can provide the sensor signal with detectable strain oscillation information over relatively large flow rate velocity ranges. Thus, the sensor can provide accurate flow rate measurements, and is very sensitive to flow rate changes.

Also, for example, the substantially T-shaped body, such as the present embodiment, is an optimum bluff body configuration to generate strain. The deflection of the rectangular plate-like section of the bluff body 2B can be relatively high. Besides, The T-shaped body is also the only shape that can be used to connect a series of flow meters with one fiber. Further it as been found that this shape can provide a very good signal-to-noise ratio of the sensor signal during operation.

In a further embodiment, the fibre part that has been joined with the vortex shedder 2 can comprise other fiber Bragg gratings, for example to detect temperature. In an embodiment, the vortex shedder 2 can be provided with a second fiber Bragg grating FBG2 of the fiber Bragg grating sensor system 3, 7, the second fiber Bragg grating FBG2 being configured to vary a respective fiber Bragg grating sensor signal as a result of perceiving temperature variations. To this aim, a longitudinal direction of the second fiber Bragg grating FBG2 preferably extends substantially perpendicular with respect to a longitudinal channel direction.

For example, the extra-second-grating FBG2 can be located a shedder location that is not substantially affected by the Karman vortices V. In FIG. 5 two possible locations for a temperature grating are indicated by arrows FBG2. For example a second fiber grating FBG2 can be provided in a mentioned first section 8a of the curved fiber part 8, or near the entry (and optionally also exit) point near the channel wall 11.

Alternatively, the assembly can be provided with another optical fiber, that does not include a mentioned first grating FBG, but does include a second grating and holds the second grating in the fluid flow to detect fluid temperature.

Besides, according to a further embodiment, the present invention can be used in mass flow determinations, for example following the teachings of the publication "A study of mass flow rate measurement based on the vortex shedding principle" H. Zhang et al., Flow Measurement and Instrumentation 17 (1), 2006, utilizing measurement results of a pressure sensor (not shown in the present application) located upstream with respect to the shedder 2 (and being spaced-apart from the shedder 2).

According to an advantageous embodiment, the present invention provides an apparatus configured to measure a physical quantity, for example the density, of the flowing fluid. In a preferred embodiment, the apparatus is provided with the flowmeter 1 that has been described above, or a similar flowmeter, and that is depicted in FIGS. 1-7.

Referring to the drawings, the apparatus includes the sensor body 2 that is configured to extend into the flowing fluid (flowing through the channel C during operation). Thus, in the present example, the sensor body 2 advantageously comprises the rigid part 2A to connect the sensor body to the wall 11 of the fluid channel. Particularly, the second part 2B of the detector body 2 is a flexible (plate-like), resilient element 2B, carrying the fiber Bragg gratings FBG, FBG2. The flexible, resilient element 2B is connected to the rigid part 2A, and an optical fibre that includes the fiber Bragg grating FBG passes through the rigid part 2A to the flexible part 2B. As follows from the drawing, the flexible element 2B extends in parallel with a flow path of the fluid (during operation). In the present example, flexible part 2B is a resilient element, extending from the rigid support part 2A.

Figure 9:
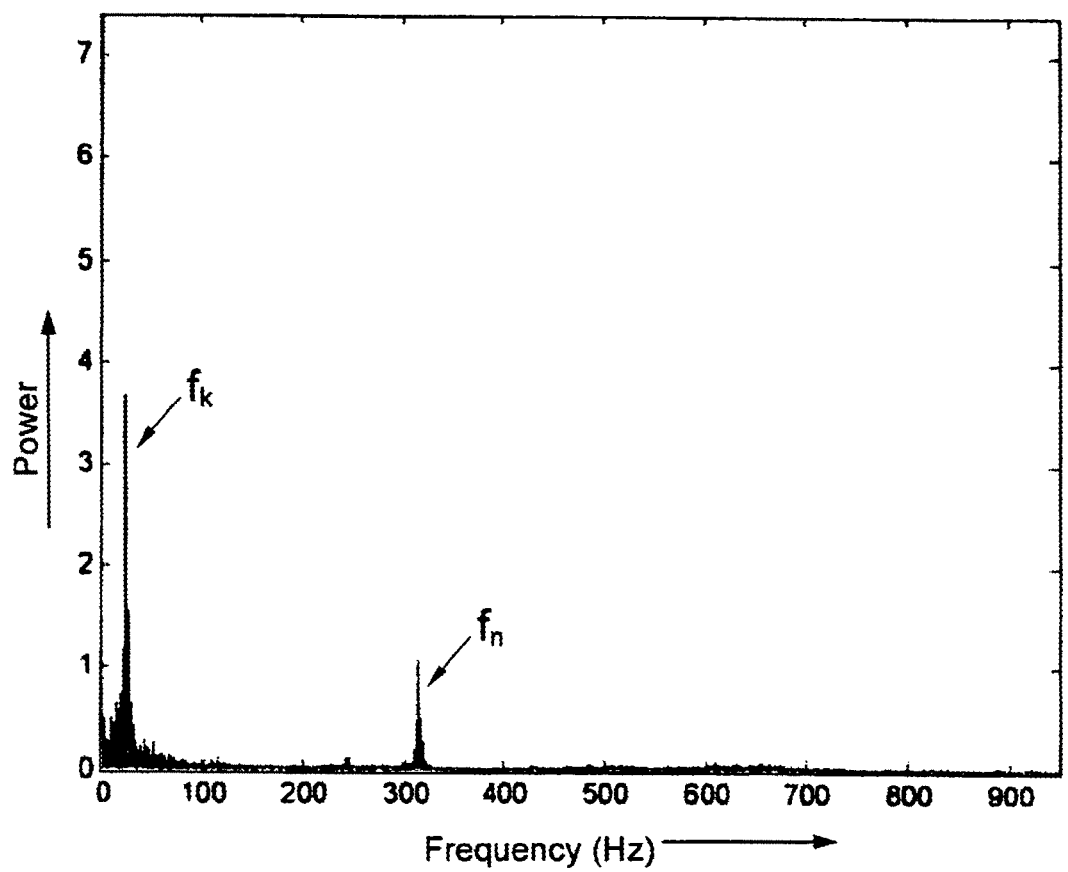
FIG. 9 depicts a graph of a measurement result, including a detected first mode natural vibration of part of the embodiment of FIGS. 1-7.

Again, the detector body 2 integrally comprises the (first) fiber Bragg grating FBG of the fiber Bragg grating sensor 3, 3 FBG, for generating a detector signal relating to vibration of at least part 2B of the sensor body 2. The apparatus includes the processing unit 3, which—in the present example—is advantageously configured to process the detector signal, and to determine the physical quantity based on detected vibration at a mechanical eigenfrequency (i.e. natural frequency) of the flexible second part 2B of the sensor body 2. In other words: the processing unit 3 is advantageously configured to detect said mechanical eigenfrequency, preferably (but not necessarily) real-time (particularly using the detector signal). An example of a frequency spectrum of detector signal is depicted in FIG. 9; obtaining such a frequency spectrum is common general knowledge (for example using Fourier Transform).

In the present example, the eigenfrequency to be detected is the frequency of a natural vibration that is mainly in lateral directions of the second shedder part 2B, i.e., in the same direction as the vortex shedding vibration (perpendicular to the fluid flow direction, as indicated by double arrow q in FIG. 3) As is mentioned before, such vibrations lead to surface strain in the second shedder part 2B, which is detected using the first fiber Bragg grating FBG The eigenfrequency of a flexible, resilient, element (connected to a rigid support) is the frequency at which the element vibrates by itself, after it has been released from a position that deviates from an initial non-vibrating state. Generally, every object has one or more eigenfrequencies (a first mode eigenfrequency having the lowest value in Hz). As follows from the following equations, the eigenfrequency depends on the density of fluid (if any) that contacts the element.

In the present non-limiting example, the eigenfrequency (natural frequency) of the flexible, resilient, part 2B of the sensor body 2 is defined by:

$$f = f_0 \cdot (1 + CK \cdot rho)^{-1/2} \quad (3)$$

wherein f is the (actual) eigenfrequency (Hz) of the flexible part 2B in the fluid, $f_0$ is an initial natural eigenfrequency (Hz) of the plate-like part 2B in vacuum, rho is the density of the fluid (kg/m$^3$) and CK is a constant (m$^3$/kg) associated with the dimensions and mass of the flexible part 2B.

The initial natural eigenfrequency $f_0$ is defined by (see "Flow-Induced Vibrations—An Engineering Guide", Naudascher and Rockwell, Dover Publications, NY2005):

$$f_0 = \frac{C^2}{2\pi G^2} \sqrt{\frac{E \cdot I_{2B}}{\mu}} \quad (4a)$$

$$I_{2B} = (L2 \cdot k^3)/12 \quad (4b)$$

wherein C is a constant, G and L2 are the afore-mentioned width and length of the part 2B (m), E is the Young's modulus (Pa) of the part 2B, $I_{2B}$ is the second moment of inertia, of μ is the mass per unit length (kg/m) of part 2B.

It follows that the eigenfrequency changes as the density of the fluid changes (an "added mass" effect). The resilient shedder part 2B accelerates part of the surrounding medium as it vibrates. This effectively raises the mass of the part 2B, decreasing its eigenfrequency.

In the present embodiment, the afore-mentioned eigenfrequency is an eigenfrequency of the flexible, resilient, element 2B. In a further embodiment, the eigenfrequency of the vibrating sensor body part 2B (to be detected) can have a value lower than 10000 Hz, particularly lower than 2000 Hz, for example lower than 1000, particularly lower than 500 Hz, or in the range of 500-1000 Hz. For example, the eigenfrequency, to be detected, can be a first-mode eigenfrequency, or a higher mode eigenfrequency (for example a second mode or third mode eigenfrequency). Preferably, said eigenfrequency is higher than an afore-mentioned vortex shedding frequency $f_K$.

Also, in a preferred embodiment, for reducing the second moment of inertia, the thickness k of the second shedder part 2B can be smaller than 4 mm, for example smaller than 2 mm, for example about 1 mm or smaller, and for example larger than 0.1 mm. As an example, the thickness k can be in the range of about 1-2 mm, or in the range of about 0.1-1 mm.

Particularly, the processing unit 3 is configured to detect deviation of the natural vibration (eigenfrequency) of the flexible second part 2B of the sensor body 2 (contacting the flowing fluid during operation) with respect to an initial eigenfrequency of the part 2B. The initial eigenfrequency can be a predetermined initial eigenfrequency, the initial eigenfrequency for example being the predetermined natural frequency $f_0$ of vibration of the resilient sensor body part 2B in a vacuum (or in a fluid). In an example, the processing unit 3 can be provided (have or be associated with) a memory, configured for storing the initial eigenfrequency of the flexible part 2B.

In another embodiment, the apparatus can be configured to detect a change of the density of the fluid (or another physical quantity of the fluid), by detecting a shift of the (instantaneous) eigenfrequency of the second shedder part 2B. For example, the apparatus can be used to measure density variations (without determining the density as such). In case only a variation of a fluid related quantity (such as density) is to be detected, it is not required to actually know any predetermined eigenfrequency (such as the eigenfrequency in vacuum) of the resilient sensor part 2B; in that case, just deviations in the eigenfrequency will have to be monitored during operation (see above equation 3).

Generally, the apparatus includes or is associated with a vibration inducer, configured to induce vibration of the flexible part 2B of the sensor body 2 using the flowing fluid. In the present examples, the vibration inducer as such operates without using external electrical power (in any case, no electric power is applies in and near the sensor body 2). Also, in the present embodiments, the vibration inducer is not configured to effect resonance of the flexible part 2B of the sensor body 2 (i.e., during operation, the flexible part 2B is not set in resonance with a dedicated resonator device). To the contrary, in the present examples, it is the fluid flow that acts on the flexible part 2B, in this case via the vortices, thereby inducing the occurrence of natural mechanical eigenfrequency vibration of the part 2B.

In the present example, during operation, the Karman vortex frequency $f_k$ of vortices V generated by the vortex shedder 2 is detectable utilizing the fiber Bragg grating sensor signal relating to the respective integral first fiber Bragg grating FBG of the vortex shedder 2. Also, preferably, the Karman vortex frequency $f_K$ is lower than the natural frequency (particularly a first mode eigenfrequency) of the second shedder part 2B.

Operation of the present example provides a method of measuring the physical quantity, in this case the density, of the flowing fluid. In use, the fluid induces vibration of a flexible part 2B of a sensor body 2 at it's eigenfrequency. At least one eigenfrequency (at least the value therefore) is being detected. The detected eigenfrequency is processed (by the processing unit 3) to determine (measure) the density of the fluid.

Particularly, the vortices V lead to the flexible part 2B vibrating at a vortex shedding frequency that is lower than the eigenfrequency; preferably, the vortex shedding frequency is detected as well by the processing unit (using the same Bragg grating FBG), so that the fluid flow rate can be determined in addition to the density of the fluid.

Example

An apparatus as is depicted in FIGS. 1-7 was used to detect the density of a fluid, in this case air (at a temperature of 20° C.), flowing through the channel C at a flow rate of 3.0 m/s. The apparatus was provided with a relatively thin, resilient shedder plate part 2B, made of stainless steel. The following parameters were used: flexible plate width G=36 mm; plate length L=80 mm; plate thickness k=0.5 mm; and density plate material=7700 kg/m$^3$.

FIG. 9 depicts a result, which is a frequency spectrum of the optical signal (received by the processing unit 3), including a peak of the detected eigenfrequency $f_n$ (at about 300 Hz in this example) of the second shedder part 2B in combination with a detected vortex shedding frequency $f_k$. The two frequency peaks are separated well (by at least 100 Hz), and can therefore be accurately and reliably processed (by the processing unit), to determine both the fluid density and the fluid flow rate. It was found that a change of density of the fluid led to a change of the detected eigenfrequency $f_n$ according to above formula (3). Thus, said formula (3) can be used—by the processing unit—to determine the density of the fluid, using the detected actual eigenfrequency (and the predetermined initial frequency $f_0$).

Other tests have been carried out of an embodiment of the invention, using natural gas in pressures from 10 to 40 bar, where the first eigenfrequency mode of the shedder plate part 2B was excited at gas velocities above 2 m/s; it was found that the eigenfrequency was directly related to gas density.

Although the illustrative embodiments of the present invention have been described in greater detail with reference to the accompanying drawings, it will be understood that the invention is not limited to those embodiments. Various changes or modifications may be effected by one skilled in the art without departing from the scope or the spirit of the invention as defined in the claims.

It is to be understood that in the present application, the term "comprising" does not exclude other elements or steps. Also, each of the terms "a" and "an" does not exclude a plurality. Any reference sign(s) in the claims shall not be construed as limiting the scope of the claims.

The shedder/bluff body 2 can be dimensioned in various ways and can have various shapes. For example, the first shedder part can have a substantially triangle-shaped cross-section, truncated triangle-shaped cross-section of a different cross-section.

Also, for example, the first part 2A of the bluff body 2 can be attached with only one end to a channel wall 11, or with opposite ends if desired.

Also, a vibration inducer can be configured in various ways. For example, in an embodiment, the flexible (resilient) part of a sensor body can be provided with a fluid drag structure, for example a relief, drag enhancing fins, of other vibration inducing means, configured to induce vibrations (including eigenfrequency vibrations) of that part using fluid drag force (of fluid, flowing along the resilient sensor part). Also, for example, vortex shedding, to effect mechanical eigenfrequency vibrations of a sensor part, is preferred, but not essential. As has been mentioned before, it is believed that the mechanical eigenfrequency vibration is excited by turbulent fluctuations naturally present in the flow, and not necessarily by vortex shedding.

The invention claimed is:

1. Apparatus configured to detect a physical quantity of a flowing fluid, the apparatus including:
   a sensor body configured to extend into the flowing fluid and comprising a fiber Bragg grating sensor, for generating optical detector signals relating to fluid induced vibrations of a flexible part of the sensor body, the fluid induced vibrations including both a vortex shedding frequency and a mechanical eigenfrequency; and
   a detector signal processing unit, configured to detect the optical detector signals and determine both the flow rate of the fluid from the vortex shedding frequency and the physical property of the fluid from the mechanical eigenfrequency, based on the vortex shedding frequency and the mechanical eigenfrequency of the flexible part being within a same frequency spectrum of the optical detector signals and a separation between the mechanical eigenfrequency and the vortex shedding frequency of at least 100 Hz.

2. The apparatus according to claim 1, wherein the sensor body comprises a fiber Bragg grating of the fiber Bragg grating sensor, the eigenfrequency f being an eigenfrequency of the flexible element.

3. The apparatus according to claim 1, wherein the flexible part extends in parallel with a flow path of the fluid.

4. The apparatus according to claim 1, the processing unit being configured to detect deviation of the actual eigenfrequency f of the flexible part of the sensor body from an initial eigenfrequency $f_0$ of that part.

5. The apparatus according to claim 1, wherein the processing unit has or is associated with a memory, configured for storing an initial eigenfrequency $f_0$.

6. The apparatus according to claim 1, wherein the eigenfrequency of the flexible sensor body part is lower than 10000 Hz.

7. The apparatus according to claim 1, the sensor body having a rigid part to connect the sensor body to a wall of a fluid channel, wherein the flexible part includes a fiber Bragg grating being connected to the rigid part, the apparatus further comprising an optical fibre that includes the fiber Bragg grating passing through the rigid part to the flexible part.

8. The apparatus according to claim 1, including or being associated with a vibration inducer, configured to induce vibration of the flexible part of the sensor body using the flowing fluid.

9. The apparatus according to claim 1, the sensor body being a vortex shedder that is configured to generate Karman vortices in the fluid during operation.

10. The apparatus according to claim 9, wherein a Karman vortex frequency ($f_K$) of vortices generated by the vortex shedder is detectable utilizing the optical detector signals, wherein the optical detector signals include fiber Bragg grating sensor signals relating to the respective fiber Bragg grating of the vortex shedder.

11. The apparatus according to claim 10, wherein the Karman vortex frequency ($f_K$) is lower than the natural frequency of the sensor body or the flexible part thereof.

12. The apparatus according to claim 1, wherein a thickness of the flexible sensor body part is smaller than 4 mm.

13. The apparatus according to claim 1 wherein the processing unit is configured to determine the frequency spectrum of the optical detector signal.

14. The apparatus according to claim 1 wherein the physical quantity is a density (rho) of the fluid.

15. The apparatus of claim 6, wherein the eigenfrequency of the flexible sensor body part is less than 2000 Hz.

16. The apparatus of claim 12, wherein the thickness of the flexible sensor body part is less than 2 mm.

17. The apparatus of claim 1, wherein the mechanical eigenfrequency, f, of the flexible part in the flowing fluid is defined by:

$$f=f_0\cdot(1+K\cdot rho)^{-1/2}$$

wherein $f_0$ is an initial eigenfrequency (Hz) of the flexible part in vacuum, rho is the density of the fluid (kg/m$^3$) and K is a constant (m$^3$/kg) associated with the dimensions and mass of the flexible part.

18. Apparatus configured to detect a physical quantity of a flowing fluid, the apparatus including:
- a sensor body configured to extend into the flowing fluid and comprising a fiber Bragg grating sensor, for generating optical detector signals relating to vibrations of a flexible part of the sensor body, the fluid induced vibrations including both a vortex shedding frequency and an actual eigenfrequency; and
- a processing unit, the processing unit having or being associated with a memory, configured for storing an initial eigenfrequency $f_0$ of the sensor body part, corresponding to a natural eigenfrequency of the sensor body part in vacuum, the processing unit being configured to utilize the optical detector signals for detecting the vortex shedding frequency and the actual eigenfrequency of the flexible part of the sensor body, for determining a deviation of the detected actual eigenfrequency of the flexible part of the sensor body from the stored initial eigenfrequency of the flexible part,
- wherein the apparatus is configured such that the vortex shedding frequency and the mechanical eigenfrequency are within a same frequency spectrum of the optical detector signals and a separation between the vortex shedding frequency and the mechanical eigenfrequency is at least 100 Hz.

19. Apparatus according to claim 18, wherein the processing unit is configured to determine the physical quantity based on the detected deviation.

20. A method of detecting a physical quantity of a flowing fluid, the method comprising inducing vibrations of a flexible part of a sensor body at both a first frequency, corresponding to a vortex shedding frequency, and an eigenfrequency the method further comprising detecting optical detector signals relating to both the vortex shedding frequency and mechanical eigenfrequency, and determining both the flow rate of the fluid from the vortex shedding frequency and the physical quantity of the fluid from the mechanical eigenfrequency, wherein the mechanical eigenfrequency and the vortex shedding frequency of the flexible part are within a same frequency spectrum of the optical detector signals and a separation between the mechanical eigenfrequency and the vortex shedding frequency is at least 100 Hz.

21. The method according to claim 20, including: inducing vortices that lead to the flexible part vibrating at the vortex shedding frequency, wherein the vortex shedding frequency is lower than the eigenfrequency.

22. The method according to claim 21, wherein the vortex shedding frequency and eigenfrequency are detected using a same sensor.

23. The method according to claim 20, wherein the optical detector signals relating to the vortex shedding frequency and the eigenfrequency are detected using a fiber Bragg grating.

24. The method according to claim 20, the method including:
- providing a sensor body that extends into the flowing fluid, the sensor body comprising a fiber Bragg grating of a fiber Bragg grating sensor, that generates the optical detector signals relating to the vortex shedding frequency and mechanical eigenfrequency of the flexible part, wherein the mechanical eigenfrequency, f, of the flexible part in the flowing fluid is defined by:

$$f=f_0\cdot(1+K\cdot rho)^{-1/2}$$

wherein $f_0$ is an initial eigenfrequency (Hz) of the flexible part in vacuum, rho is the density of the fluid (kg/m$^3$) and K is a constant (m$^3$/kg) associated with the dimensions and mass of the flexible part.

25. The method according to claim 20, including:
- providing a sensor body that extends into the flowing fluid, the sensor body comprising a fiber Bragg grating of a fiber Bragg grating sensor, that generates the optical detector signals; and
- processing the optical detector signals for detecting the mechanical eigenfrequency of the flexible part of the sensor body; and
- determining a deviation of the detected eigenfrequency of the flexible part from a predetermined initial eigenfrequency of the flexible part.

26. The method according to claim 25, wherein the processing includes the use of a frequency spectrum of the optical detector signal.

27. The method of claim 26, wherein the processing includes the detection of a peak in said frequency spectrum, which peak is associated with said actual mechanical eigenfrequency.

28. The method according to claim 20, wherein the eigenfrequency is lower than 1000 Hz.

29. The method of claim 20, wherein the physical quantity is density.

* * * * *